United States Patent [19]

Sonnenschein et al.

[11] Patent Number: 4,859,585

[45] Date of Patent: Aug. 22, 1989

[54] IN-VITRO METHODS FOR IDENTIFYING COMPOSITIONS WHICH ARE AGONISTS AND ANTAGONISTS OF ESTROGENS

[75] Inventors: Carlos Sonnenschein; Ana M. Soto, both of Boston, Mass.

[73] Assignee: Trustees of Tufts College, Medford, Mass.

[21] Appl. No.: 853,240

[22] Filed: Apr. 17, 1986

[51] Int. Cl.$^4$ ............................................. C12Q 1/02
[52] U.S. Cl. .................................................. 435/29
[58] Field of Search .......................................... 435/29

[56]  References Cited

PUBLICATIONS

Coezy et al, Cancer Research, 42, 317–323, 1982.
Reddel et al, Cancer Research, 43, 4618–4624, 1983.
Soto et al, Biochem. Biophys. Res. Communic., 122, 1097–1103, 1984.
Biotechnology, Fisher Scientific, 1983, p. 97.
Sonneschein et al, J. Cell Biol., 99, 3392, 1984.
Sonneschein et al, Biol. Abstr., 80, Abstr. No. 69567, 1985.
Stack & Gorski, Endocrinology, 115: 1141–1150 (1984).
Sonnenschein & Pierce, Cancer Research, 41: 4742–4743 (1981).
Laugier et al., Proc. Natl. Acad. Sci. USA, 80: 1621–1625 (1983).
Soto & Sonneschein, J. Cell Biol., 97: 393a (1983).
Soto & Sonneschein, Proc. Am. Assoc. Can. Res., 25: 213 (1984).
Schatz et al., Endocrinology, 115: 501–506 (1984).
Paz et al., J. Cell Biol., 99: 339a, No. 1256 (1984).
Sonnenschein & Soto, Proc. AACR, 26: 198, No. 783 (1985).
Soto et al., Proc. AACR, 26: 198, No. 784 (1985).
Soto & Sonnenschein, Endo. Soc., 67th Annual Mtg., No. 1152 (1985).
Sonnenschein & Soto, Endo. Soc., 67th Annual Mtg., No. 663 (1985).
Sonnenschein et al., Life Sciences, 37: 387–394 (1985).
Soto & Sonnenschein, J. Steroid. Biochem., 23: 87–94 (1985).
Schatz et al., J. Cell. Physiol., 124: 386–390 (1985).
Papendorp et al., J. Cell. Physiol., 125: 591–595 (1985).

Primary Examiner—Esther M. Kepplinger
Assistant Examiner—David A. Saunders
Attorney, Agent, or Firm—David Prashken

[57] ABSTRACT

The present invention provides two general protocols by which a substance may be identified and characterized as an estrogen agonist and/or an estrogen antagonist. The protocols are in-vitro methods which utilize estrogen dependent cells in culture and a medium comprising an inhibitor endogenous to the sera of adult humans which is able to prevent the proliferation of cultured cells in-vitro. The methodology is rapid, reproducible, accurate and provides the major advantage of being able to screen large numbers of substances for their primary or secondary side effects in a large variety of medical and environmental applications.

13 Claims, 6 Drawing Sheets

FIG. 1

O = POSITIVE CONTROL (CELLS+ESTRADIOL+CDHS)
● = NEGATIVE CONTROL (CELLS+CDHS, WITHOUT ESTRADIOL)
⬢ = PARTIAL ANTAGONIST (CELLS+ESTRADIOL+TEST SUBSTANCE)
⬡ = FULL ANTAGONIST (CELLS+ESTRADIOL+TEST SUBSTANCE)

♦ = CELLS + INHIBITOR PREPARATION
○ = CELLS + INHIBITOR PREPARATION + ESTRADIOL

IN-VITRO METHODS FOR IDENTIFYING COMPOSITIONS WHICH ARE AGONISTS AND ANTAGONISTS OF ESTROGENS

FIELD OF THE INVENTION

The present invention is concerned generally with methods for identifying chemical compositions whose pharmacological activities mimic or contradict the action of naturally occuring estrogens and is particularly directed to in-vitro protocols which will classify pharmacologically active compositions as being either full or partial agonists and/or full or partial antagonists of estrogens.

BACKGROUND OF THE INVENTION

Naturally occurring or endogeneous estrogens constitute one class of steroid sex hormones which are produced in the ovaries and other tissues in the body and which stimulate the growth and development of the secondary sex characteristics in female animals. The naturally occuring estrogens are estrone (also known as $E_1$), estradiol-17B (also known as $E_2$), and estriol (also known as $E_3$) The secretion of such estrogens controls in major part the normal sexual cycle in humans and animals which appears characteristically as the changes of estrus, a period of mating activity marked by intense sexual urge (sexual heat).

Historically, it has been demonstrated that removal of both ovaries from an adult normal female mammal abolishes estrus, that is the period of intense sexual urge and mating activity; equally important, it was found that entering into the state of estrus is accompanied and characterized by visually identifiable and distinct changes in the cell structure of the cells lining the vagina. At the height of estrus, the cell lining acquires a unique, cornified character easily distinguishable from those cells present when the animal is resting, in a nonestrus condition, in an immature animal which does not display full sexual activity of an adult, or has been castrated. On this historical and technical basis, the naturally occurring estrogens were first isolated and purified. Concomittantly, the term "estrogen" is defined only in operational form as—any substance able to induce estrus in a living animal. In consequence, all other pharmacologically active compositions, steroidal and nonsteroidal which were subsequently synthesized and which were demonstrably able to induce estrus or to mimic the induction of estrus have been conventionally classified as "estrogenic" regardless of their chemical structure or their mechanism of action.

The value of naturally occuring estrogens and synthetic compositions demonstrating "estrogenic" activity has been in their medical and therapeutic uses, many of which continue to be the subject of considerable controversy. A traditional listing of the therapeutic applications for estrogens alone or in combination with other active agents includes: oral contraception; relief for the symptoms of menopause; prevention of threatened or habitual abortion; relief of dysmenorrhea; relief of dysfunctional uterine bleeding; an aid in ovarian development; treatment of acne; diminution of excessive growth of body hair in women (hirsutism); the prevention of heart attacks; treatment of osteoporosis; an alternative to surgery for metastatic breast cancer; treatment of prostatic carcinoma; and suppression of post-partum lactation [Goodman and Gilman, *The Pharmacological Basis Of Therapeutics* (Seventh Edition), Macmillan Publishing Company, 1985, pages 1421-1423]. Accordingly, there has been increasing interest in finding newly synthesized compositions and new uses for previously known compounds which are demonstrably estrogenic, that is, able to induce estrus. Probably the best known examples are: ethinyl estradiol (Estinyl); 3-methyl-ethinyl estradiol (Mestranol); and diethylstilbestrol (DES); methallenestril (Vallestril); and doisynoestrol (Fenocylin).

Despite the apparent wide interest in compositions said to be estrogenic, surprisingly few assay methods are available to detect and identify those compositions which have the pharmacological ability to initiate estrus. To date, only three are recognized: the cornification of vaginal cells in the spayed rodent; the change in weight of excised wet uterine tissue; and the ability of the composition to bind competitively with radiolabeled estradiol in cytosol preparations, and homogenates of immature uterine cells. Each of these will be briefly summarized.

The cornification of vaginal cells is the classical methodology by which the naturally occurring endogenous estrogens were discovered. The assay methodology has remained substantially unaltered since its first use [Allen and Doisy, *J. Am. Med. Assoc.* 81:819 (1923)]. The assay is based upon the ability of a substance to produce the typical estrus response in-vivo when injected into castrated rats or mice. A positive reaction is characterized by the distinct change in the structure of the cells lining the vagina in which the cells acquire a unique, cornified appearance easily distinguishable from cells in the resting state. Microscopic examination of vaginal smears provides empirical evaluation of the estrus condition of the living animal. Traditionally, the activity of a substance under test is expressed in terms of mouse or rat units. A mouse unit is the quantity of endogenous estrogen that just suffices to produce estrus in a castrated animal. Typically, the mouse unit varies from about 0.04–0.1 microgram (hereinafter "ug") of pure estrone; the international unit of activity has been set as 0.1 ug of estrone.

The uterine wet weight assay identifies substances which induce estrus by measuring the increase in the mass weight of uterine tissues, the increase in weight being directly attributable to the interaction between those substances and the secondary sex organs. The test utilizes immature and/or adult ovariectomized mice and rats which are administered a test substance subcutaneously using an inert fluid such as corn oil. Groups of six to ten animals are typically injected daily for three days with the putative estrogenic substance and sacrificed on the fourth day. The uteri are removed, dissected free of extraneous tissue and the fluid contents expelled. Each excised uterine tissue is then blotted and the wet weight determined individually. The increased wet weight of the uterine tissue in comparison to those from control animals receiving only the inert fluid identifies a potent estrogenic composition [Astwood, *Anat. Rec.* 70:5 (1938); Kay et al., *Biochem. Biophys. Acta.* 261:475 (1972); Black et al., *Life Sciences* 26:1453-1458 (1980)].

The competitive binding assay is based on the existence of a specific estrogen receptor (hereinafter "ER") on the cell or tissue extract to which all putative estrogenic compositions will specifically bind in some measurable degree. The binding of the substance to the ER site is believed by many investigators to be responsible for initiating both protein synthesis and cell proliferation in those cells and tissues having demonstratable ER sites. Although initially described as an in-vivo technique [Jensen and Jacobson, *Rec. Prog. Horm. Res.* 18:387–414 (1962)] the preferred technique is an in-vitro methodology in which binding of the estrogenic substance occurs in a homogenate of rat uterine tissue which has been prepared as a cytosol, the supernatant fraction containing the soluble proteins after sedimentation at 105,000×gravity for one hour [Noteboom and Gorski, *Arch. Biochem. Biophys.* 111:559–568 (1965); Talwar et al., *Proc. Natl. Acad. Sci. U.S.A.* 52:1059–1066 (1964)]. This supernatant fraction, the cytosol, is typically combined with the test substance for 30 minutes at 4° C. in a test tube. Controls are prepared using inert fluid carriers and non-specific binding is determined in parallel preferrably using a synthetic estrogen such as DES. Subsequently, radiolabeled [$^3$H] estradiol is added to all samples at a predetermined concentration. The incubation is continued after which a suspension of dextran-coated charcoal in a suitable buffer is added to all the samples and allowed to react for approximately 20 minutes' duration. Each control and test sample is then centrifuged to yield a discardable precipitant and a supernatant whose radionuclide content is measured by liquid scintillation counting. [Jordan et al., *J. Endocr.* 75:305–316 (1977)].

It is noteworthy that all the presently accepted assay techniques, whether in-vivo or in-vitro, are based upon a single common mechanism of action for all estrogens as a class (including endogeneous estrogens, synthetically prepared estrogens and other substances demonstrating estrus inducing activity). The theory accepted almost exclusively is the existence of putative intracellular receptor proteins for the estrogenic substance in the cells of estrogen responsive tissues such as the vaginal lining, uterine tissue, the female breast, the pituitary, and the hypothalamus. Estrogens and estrogenic compositions bind with high affinity to the intracellular receptor protein, termed the estrogen receptor or "ER" site. After binding the formed estrogen-protein complex is said to be converted into a species that is physically translocated to the nucleus of the cell where further binding of the estrogen to the genetic material occurs. Some recent publications have confirmed the data reported previously [Mester et al., *Exp. Cell Res.* 81:447–452 (1973)] suggesting that estrogens bind directly to unoccupied nuclear ER sites avoiding the translocation step [King and Greene, *Nature* 307:745–747 (1984); Welshons et al. *Nature* 307:747–749 (1984)]. Subsequent to these events, a general increase cell proliferation is observed. [Gorski and Gannon, *Annu. Rev. Physiol.* 38:425–450 (1976); Gorski et al., *Recent Prog. Horm. Res.* 24:45–72 (1968); Jordan, *Pharmacological Reviews* 36:245–276 (1984)].

It is ironic that the effort to procure new estrogenic compositions and to obtain evidence which reinforces the hypothesis that a single ER site for estrogen is present in estrogen sensitive cells and tissues has led directly to the recognition and isolation of several different kinds of compounds that in fact inhibit or neutralize the action of endogenous estrogens. These have been termed "antiestrogens". Historically, the weakly estrogenic compound chlorotrianisene, unlike most estrogens, was observed not to cause enlargement of the pituitary when given to rats in large doses. Estrogens normally cause pronounced enlargement of the pituitary, but when chlorotrianisene was given concurrently with estradiol, the effect was greatly reduced [Segal and Thompson, *Proc. Soc. Exp. Biol. Med.* 91:623–625 (1956)]. Subsequently, the related non-estrogenic compound, ethanoxytriphenol, was found to be strikingly antiestrogenic. It inhibited the activity of endogeneous estrogen as well as of synthetic estrogens such as DES and chlorotrianisene. Subsequently, a large number of other antiestrogens have been identified and classified according to their chemical structure into two different classes: steroidal antiestrogens such as RU16117 which dissociates rapidly from the ER site and RU39411 which forms a more stable complex with the ER protein; and non-steroidal antiestrogens including the triphenylethylenes such as tamoxifen and its various derivatives, enclomiphene, clomiphene, nafoxidine, LY117018 and Keoxifene [Jordan, V., *Pharmacological Reviews* 36:245–276 (1984); Jordan et al., *Cancer Treat. Rep.* 64:745–759 (1980); Heel et al., *Drugs* 16:1 (1978); Legha et al., *Ann. Intern. Med.* 88:69–77 (1978)].

An "antiestrogen" is usually defined as a compound that will inhibit the vaginal cornification produced by estradiol in ovarectomized rats and/or will inhibit the increase in uterine weight produced by estradiol in immature rats. The existence of a specific antiestrogenic binding site in addition to the traditionally accepted ER binding site on specific cells and tissues has been an area of intense controversy and study. Solely to test this theory, two in-vitro test systems have been developed: the growth of MCF-breast cancer cells - to specifically determine the effects of tamoxifen and its metabolites on cell proliferation [Coezy et al., *Cancer Res.* 42:317–323 (1982); Reddel et al., *Cancer Res.* 43:4618–4624 (1983)] and estrogen-stimulated prolactin synthesis by primary cell cultures of immature rat pituitary glands—for the ability of antiestrogens to inhibit prolactin synthesis [Lieberman et al., *J. Biol. Chem.* 258:4734–4740 (1983); Lieberman et al., *Proc. Natl. Acad. Sci. U.S.A.* 75:5946–5949 (1978)].

The ability to identify and to distinguish between estrogenic compounds and antiestrogens is recognised as critical by physicians and pharmacologists. Naturally occurring endogenous estrogens are able to induce a variety of multiple changes in their target organs: increased cellular proliferation or hyperplasis; induction of specific protein synthesis; and an increased cellular mass or hypertrophy. From the viewpoint of clinicians and human disease, the hyperplastic effects are the most important because it is central to the problem of hormone-sensitive cancers and their control. Estrogen antagonists thus are of primary interest. From the viewpoint of pharmacologists interested in developing new drugs useful for the treatment of human diseases and specific pathological conditions, it is most important to procure compounds with some demonstrable estrogen-like function but which are devoid of proliferative side-effects. Exemplifying this latter view, osteoporosis, a disease in which bone becomes increasingly more fragile, is greatly ameliorated by the use of fully active estrogens; however, due to the recognized increased risk of cancer in patients chronically treated with active estrogens, it is not clinically advisable to treat osteoporosis with fully active estrogens. Accordingly estrogen agonists are the primary interest and focus.

The difficulties of identifying and evaluating estrogen agonistic compositions and estrogen antagonistic compounds are recognized. In-vivo methods to detect and identify such compositions have been difficult to perform in a consistent manner and are open to independent biological variations which cannot be entirely controlled or eliminated. Equally recognized as a continuing problem are the mechanisms of action for estrogenic and antiestrogen compositions—the evidence for which is often conflicting, extremely complex, and frequently inconsistent. Each class of composition has been shown to have different properties in estrogen target tissues and to induce radically different pharmacological reactions among alternate species of test animals. The best example of the latter is the number of estrogenic and antiestrogenic compositions which have been demonstrated to be active in rats and mice but which have subsequently been found to be inactive or poorly effective in clinical trials using human subjects. Underlying and inherent in each of these problems and difficulties, is the seemingly widely accepted requirement to conform to the generally accepted theory of intracellular ER sites on the target cells and tissues before any in-vivo or in-vitro assay methodology may be deemed effective. As can be readily appreciated, there is a continuing need for novel, reliable, accurate, and sensitive assay protocols which will identify those pharmacological substances which are demonstrably active as estrogens from those which are inhibitors or neutralizers of estrogens and from those substances which are completely quiescent with respect to estrogens.

SUMMARY OF THE INVENTION

The present invention comprises in-vitro methods for identifying and characterizing a test substance as an estrogen agonist and as an estrogen antagonist. The method for identifying an estrogen agonist comprises the steps of obtaining a plurality of cells cultured in-vitro, these cells being estrogen dependent for proliferation in-vivo; maintaining a known quantity of these cultured cells in a medium comprising a fluid and an inhibitor endogenous to the sera of adult humans, this endogenous inhibitor being present in the medium at a concentration effective to prevent proliferation of the cells in-vitro; adding the test substance to the cultured cells and the maintaining medium to form a reaction mixture; incubating the reaction mixture for a preselected period of time; and determining the number of cultured cells in the incubated reaction mixture, a measurable increase in the number of cultured cells serving to identify the test substance as an estrogen agonist.

The general method for identifyinq an estrogen antagonist comprises the steps of obtaining a plurality of cells cultured in-vitro, these cells being estrogen dependent for proliferation in-vivo; maintaining a known quantity of these cultured cells in a medium comprising a fluid and an inhibitor endogenous to the sera of adult humans, the endogenous inhibitor being present in the medium at a concentration effective to prevent proliferation of the cells in-vitro; adding the test substance and an active estrogen to the cultured cells and the maintaining medium to form a reaction mixture; incubating the reaction mixture for a preselected period of time; and determining the number of cultured cells in the incubated reaction mixture, the failure of said cultured cells to measurably increase in number serving to identify the test substance as being an estrogen antagonist.

Although each method comprising the invention may be performed to advantage individually and independently, it is preferred that both general methodologies be performed concurrently or sequentially in order to obtain the broader range of information and data about the substance being evaluated. In addition, the methodology is rapid, technically easy to perform, and provides meaningful data in a precisely controlled in-vitro assay environment.

DETAILED DESCRIPTION OF THE FIGURES

The present invention may be more easily and completely understood when taken in conjunction with the accompanying drawing, in which.

DETAILED DESCRIPTION THE PREFERRED EMBODIMENTS

The present invention is a general, in-vitro test methodology which is used in alternative modes and provides distinct protocols for the identification and characterization of unknown substances for their capacity to serve as agonists and/or antagonists of endogenous estrogens.

There are multiple advantages provided by the methodologies comprising the present invention. These include:

1. The ability to identify available or newly synthesized compounds as estrogen agonists and/or estrogen antagonists in a verifiable and reproducible manner within a controled in-vitro assay environment. All of the experimental parameters and factors are predetermined and carefully prepared to lie within selected limits—thereby eliminating the effects of individual biological variation common to all in-vivo studies.

2. The capability to test statistically significant numbers of different substances over a relatively short period of time. Although the optimal time for each test is ten days in duration, each day's testing is performed in staggered series; accordingly, several hundred individual test samples can be prepared within one average working day and a different compound can be tested each day following in succession. Over a two week time period, at least five different days' testing can be empirically evaluated.

3. The means for reducing the present costs of testing are provided by each protocol of the present invention. In comparison with present in-vivo animal studies and their concomitant high cost per animal, their limited availability in numbers, and their inconvenience (housing, maintenance, and handling), the described in-vitro methods are very inexpensive to perform. Furthermore, in view of the major budget constraints now commonly in effect as a limiting factor in the realization of bringing a new therapeutic composition to market, the present invention offers a cost-effective procedure for evaluating the many presently synthesized compounds which were considered marginal and thus unlikely of ever being evaluated via in-vivo testing.

4. The means for correlating the pharmacological properties of the substance under test directly with its individual structural organization and chemical formulation. The protocols of the present invention are completely unlike the known in-vivo assay method and do not rely upon the appearance of gross anatomical changes such as cornification of vaginal cells or the increase in weight of excised uterine tissues. Moreover, unlike the competitive protein binding assays, the described protocols are not based upon the pre-existence of identifiable estrogen receptors proteins and do not require that ER-induced new protein synthesis be directly linked with cell proliferation. The present invention, instead, permits the user to take into account the mechanism of action of the substance under test as it demonstrates its individual pharmacological activity; and it allows a more detailed evaluation of the structure-function relationship of the test substance.

As a result of the historical development in this art, a number of terms have come into common usage which are non-informative at best and misrepresentative and distortive in the worst instances. These terms include "estrogenic", "estrogenicity", and "antiestrogen". Equally difficult and distortive is the common practice of directly linking the ability of potent estrogens to initiate new protein synthesis in a target cell or tissue with the distinctly different ability of the active estrogen to induce cell proliferation. Contrary to this common habit, the present invention relies and depends upon the ability to separate each of these characteristic abilities and to evaluate them independently without direct interdependence between them.

To avoid confusion and miscommunication, and for greater ease and clarity of understanding of both the basis of the present invention and the major advance in this art which it represents, a set of strictly-adhered-to definitions and terms will be employed herein. It will be expressly noted, however, that the terms "estrogenic" and "antiestrogen" have no well-defined meaning and will not be used at any time in the description which follows. Instead, the following terms and definitions are employed exclusively.

Estrogens: A class of compounds including naturally occuring and synthetically made compositions which have a demonstrated ability to induce cell proliferation in-vivo and in-vitro. Cells and tissues said to be estrogen dependent are those cells and tissues which require one or more of the naturally occurring estrogens to be present for the cells and tissues to proliferate in-vivo. Synthetic estrogens mimic the characteristics of naturally occuring estrogens to induce proliferation of cells, tissues, and organs in-vivo and in-vitro. As used herein, the ability of naturally occuring estrogens and/or synthetic estrogens to induce or to fail to initiate new protein synthesis in specific targeted cells and tissues is of no consequence.

Naturally occuring estrogens: The three most common, naturally occuring estrogens are: estrone ($E_1$), estradiol-17B ($E_2$), and estriol ($E_3$). Of these, estradiol is the most active pharmacologically and is the estrogen of choice in the test methodologies comprising the present invention.

Synthetic estrogens: A class of compounds not occurring in nature which duplicate or mimic the activity of endogenous estrogens in some degree. These compounds include a variety of steroidal and non-steroidal compositions exemplified by dienestrol, benzestrol, hexestrol, methestrol, diethylstilbestrol (DES), quinestrol (Estrovis), chlorotrianisene (Tace), and methallenestril (Vallestril). The pharmacological activities of these compositions often present apparently conflicting properties. For example, DES is noted for its ability to mimic naturally occuring estrogens and has little demonstrated capacity to inhibit or neutralize the pharmacological action of naturally occuring estrogens; on the other hand, chlorotrianisene only weakly mimics the activity of naturally occuring estrogens but is demonstrated to be a potent inhibitor or neutralizing agent when combined with naturally occuring estrogens. Accordingly, following the preferred terminology and usage employed herein, DES is properly identified as a full or complete agonist with no antagonistic properties; while chlorotrianisene is properly characterized as a partial agonist and a complete antagonist of naturally occuring estrogens.

Full or complete agonist: A compound that either produces or mimics the effect of naturally occuring estrogens.

Partial agonist: A compound that either produces or mimics the effects of naturally occuring estrogens in some degree but which is markedly inferior in activity and effect to the results obtained with a full agonist even at the highest attainable dosage.

Full or complete antagonist: A compound which completely inhibits or neutralizes the effect of a naturally occuring estrogen when administered simultaneously with such an estrogen.

Partial antagonist: A compound which only partially neutralizes or inhibits the effect of a naturally occuring estrogen when administered simultaneously with that estrogen, even at the highest attainable dosage.

For purposes of the present invention, it is only the ability of naturally occurring estrogens to induce the proliferation of their target cells and tissues through an indirect mechanism of action which is of interest. For this reason, all substances under test are evaluated for proliferative activity only with respect to naturally occurring estrogens. The present invention is based upon and utilizes the empirical finding that human serum and plasma contain a demonstrable endogenous inhibitor which prevents the proliferation of estrogen dependent cells and tissues in-vivo and in-vitro [Sonnenschein and Pierce, *Cancer Research* 41:4742–4743 (1981); Soto and Sonnenschein, *J. Cell Biol.* 97:393a (1983); Paz et al., *J. Cell Biol.* 99:339a (1984); Schatz et al., *Endocrinology* 115:501–506 (1984); Soto and Sonnenschein, *Biochem. Biophys. Res. Comm.* 122:1097–1103 (1984); Soto and Sonnenschein, *Proc. Am. Assoc. Cancer Res.* 25:213 (1984)]. Each of the in-vitro methods for identification of estrogen agonists and estrogen antagonists makes use of the indirect-negative mechanism present in-vivo, in which estrogens demonstrably cancel the effect of plasma-borne specific inhibitors of estrogen-sensitive cell proliferation. The use of this specific mechanism of action, within an in-vitro methodology for the characterization of unknown test substances as agonists and/or antagonists of naturally occuring estrogens, was previously unknown and unappreciated in this art.

The present invention is preferably utilized as a combination of two different in-vitro methodologies performed concurrently or in sequence. One test methodology identifies a test substance as an estrogen agonist—that is, a test substance which duplicates or mimics the effects of naturally occuring estrogens completely or partially. The second methodology evaluates the test substance as an estrogen antagonist—that is, the ability to inhibit or neutralize a naturally occuring estrogen when both are administered simultaneously. The individual methods to identify an agonist or antagonist of estrogens employ common cells, reagents, and follow similar protocols. For this reason, the constituents commonly shared and used in both methods, albeit for different purposes and goals, will be described.

Cells

A wide variety of different cells in culture may be employed in the identification methods described herein Such cell lines are maintained by tissue culture methods and medium commonly available and used in the art, many of which are commercially prepared and sold. The sole essential requirement to be demonstrated by the culture cell line is the demonstrated need for a naturally occuring estrogen to be present before the cells proliferate in-vivo—that is, in their naturally occuring state within the living animal. Mammalian cell lines are preferred, with human cell lines being more preferred than cell lines from mice, rats, and the like. In addition, it is preferable in many instances that the cultured cell line be an abnormal or tumor cell line derived from cancers or tumors in the living animal. Desirable cell lines include: MCF7 cells, passage number 173 (Michigan Cancer Foundation, Detroit, Mich.) and the $C_7MCF7$-173 clone which are derived from human breast tumor cells (Tufts University, School of Medicine, Boston, MA); T47D-All cells, a clonal population from the uncloned T47D cells originally described by Keydar et al. [*Eur. J. Cancer* 15:659–670 (1979); Instituto de Biologiay Medicina Experimental, Buenos Aires, Argentina; Rockville, MD.]; and clones of the H301 cell line of the Syrian hamster kidney adenocarcinoma originally described by Sirbasku and Kirkland [*Endocrinology* 98:1260 (1976); Tufts University, School of Medicine, Boston, MA]. Each of these cultures cell lines are demonstrably estrogen dependent for proliferation in-vivo. Prior to use in the protocols of the present invention, each of the cell lines are routinely grown in 5% (v/v) fetal bovine serum (hereinafter "FBS") commercially obtained (Sterile Systems Inc., Logan, Utah) in Dulbecco's modification of Eagle's Medium (hereinafter "DME") in an atmosphere of 5% $CO_2$/95% air under saturating humidity at 37° C. At the time of test, each cell line is preferably introduced at the stated aliquot concentrations into the wells of multiwell plates (Costar 3512 plates, Cambridge, MA). The cell aliquot in each well is allowed to attach to the surface of the well for a period of 6–24 hours after which the seeding medium (5% FBS in DME) is removed and replaced by specific quantities of the maintaining medium used during the testing phases. Preferably, the fluid comprising the maintaining medium was DME supplemented with various concentrations of charcoal-dextran stripped human serum (hereinafter "CDHS"). Alternatively, one may use 2% charcoal-dextran stripped human serum supplemented with known concentrations of an active inhibitor preparation as will be described hereinafter.

Charcoal-Dextran Stripped Human Serum (CDHS)

Venous blood is drawn from healthy human adult men and women. The blood is allowed to clot on sterile 50 milliliter (hereinafter "ml") plastic tubes for approximately four hours' duration. The sera are then clarified by centrifugation (3,000 rpm for ten minutes) and subsequently "heat inactivated" (30 minutes at 56° C.), filtered through a 0.45 micron pore filter (Millipore Corporation, Bedford, Massachusetts,) aliquoted into said volumes, and stored at −20° C. for future use. Subsequently, the sera are stripped of endogenous estrogens by extraction with 0.5% charcoal in the following manner.

A 0.5% charcoal (Norit A, Acid washed, Sigma Corporation)—0.05% dextran T70 (Pharmacia Corp., Piscataway, N.J.) suspension is prepared. The charcoal-dextran aliquots in volumes similar to the volume of the serum aliquots to be processes are centrifuged at 3000 rpm for 10 minutes to pack the charcoal into a pellet. The supernatants are aspirated to yield the formed charcoal pellet. Each serum aliquot is mixed with the charcoal pellet and maintained in suspension by means of a roller apparatus set at 3 cycle/minute at 37.5° C. for 60 minutes duration. To monitor the extraction efficiency, comparable volumes of each sera are equilibrated for 16 hours at room temperature with radiolabeled estradiol at $10^{-9}M$ and $10^{-8}M$ concentrations respectively, prior to charcoal extraction. It is found that 99% of the radiolabeled estradiol is removed by this treatment.

Each of the prepared sera are combined with the charcoal pellets and are consequently stripped of endogenous estrogens via this extraction method. Subsequent testing demonstrates that the endogenous inhibitor remains stable in the treated serum even after 5 successive charcoal-dextran extractions.

Within the preferred protocols to identify agonists and antagonists of estrogens, the CDHS is added to the DME in quantities sufficient to form a final concentration ranging from 40–10% by volume. This CDHS and DME in combination comprises the preferred maintaining medium for use in the protocols. The actual concentrations of endogenous inhibitor present in the CDHS thus are also diluted in concentration to a working range of between 40–10% of its original concentration in adult human serum.

Estrogens

The estrogens preferred for use with the present invention comprised the natural endogenous estrogens (estrone, estradiol, and estriol) and their various chemical forms such as alpha-$E_2$, beta-$E_2$, and the like. If desired, it is possible to utilize any of the wide variety of synthetically made estrogens as a comparative basis. However, this latter approach is not preferred because of the wide range of steroidal and non-steroidal compositions which, although able to mimic the effect of endogenous estrogens, also demonstrate a variety of antagonistic effects. The estrogen of choice for each of the in-vitro methods to identify agonists and antagonists of estrogens is estradiol ($E_2$).

The Preferred Protocols

It is most preferred that the present invention be performed in two test phases in order that a single substance under test be evaluated and identified in terms of its agonistic and antagonistic properties with respect to estradiol. For ease and simplicity, the phase 1 test identifies agonistic characteristics; in turn, the phase 2 test identifies the antagonistic characteristics. Each test protocol will be described in detail.

Phase 1 Protocol To Identify Estroqen Agonist Properties

This protocol measures the potential agonistic properties of the substance under test. All manipulations are to be carried out under sterile conditions using disposable plastic tissue culture multiwell plates with all manipulations preferably being performed in a tissue culture hood.

1. The cell line of choice is the $C_7MCF7$-173 culture, a cloned estrogen-sensitive breast tumor cell line. The cell line is routinely grown in 5% fetal bovine serum—supplemented Dulbecco's modified Eagle minimal essential medium (hereinafter "5% FBS/DME"), at 37° C. in a 95% air—5% $CO_2$ atmosphere.

2. The cultured cells growing in 5% FBS/DME are harvested by treatment with trypsin (1:250)—EDTA (0.2%). The cells are detached by brief exposure to trypsin for five minutes. To avoid excessive proteolysis, the reaction is quenched by addition of three volumes of 5% FBS/DME. The resulting cell suspension is collected into a sterile centrifuge tube and centrifuged at 800 x gravity for five minutes' duration. The supernatant is discarded and the cell pellet resuspended in 5% FBS/DME by pipetting gently. The cell suspension thus obtained is diluted into prepared aliquots using 5% FBS/DME. Each prepared suspension preferably contains 40,000 cells in a volume of 0.10 ml and it is desirable that the number of cells be counted and verified by means of a Coulter Counter (Coulter Electronics, Hialeah, Fla.).

Subsequently, 1.0 ml aliquots of 5% FBS/DME are placed in each well of a multiwell (Costar 3512) plate. The number of wells in each plate will correspond to the number of test substances to be evaluated and thus is merely a question of choice or convenience to the user. Into each well, 25 microliter (hereinafter "ul") aliquots of the prepared cell suspension are added using a 1.0 ml syringe fitted with a 22 gauge needle attached to a repetitive Dunn pipetter (Skatron Dispenser). The microtiter plate is then gently shaken to avoid unequal cell distribution within each individual well. The seeded cells are then allowed to attach to the plastic surface of the well proper over a period of 24 hours' duration after which the fluid is changed to the experimental maintaining medium.

3. At the time of test, all the seeded cells in each well of the microtiter plate receive 20% heat inactivated—charcoal-dextran human stripped serum (CDHS) in DME at a volume of 0.9 ml per well. Although higher concentrations of CDHS may be utilized up to and including 40% concentrations, the 20% concentration is most preferred.

4. To those wells or plates designated as controls, $E_2$ is added in a range of ever decreasing concentration. Preferably, a series of controls are prepared containing: no estradiol (the negative control); $3 \times 10^{-8}$ M $E_2$; $3 \times 10^{-9}$M $E_2$; $3 \times 10^{-10}$M $E_2$; $3 \times 10^{-11}$M $E_2$; and $3 \times 10^{-12}$M $E_2$ (the positive control). Each of these respective concentrations of estradiol are achieved by adding a 10X stock solution in a preferred total volume of 100 ul of DME. If desired experimental controls having concentrations of $E_2$ up to $10^{-5}$M may be utilized to advantage. However, $E_2$ causes maximum cellular proliferation at an optimum concentration of $3 \times 10^{-11}$M. For this reason, the preferred controls contain the described concentrations of $E_2$.

5. To the other prepared (seeded) wells, 100 ul of the test substance to be evaluated is added as a 10X stock solution to achieve final concentrations ranging from $10^{-5}$M to at least $10^{-12}$M. The substance under test is preferably prepared as a stock solution in ethanol, most preferably as a $10^{-3}$M solution. All dilutions are made using DME. The ethanol concentration in the culture medium should be kept below 0.01% by volume. This preparative technique avoids the need to filter the various volumes of test substance to achieve sterility. This is particularly valuable because steroidal compositions are known to become adsorbed to the commercially obtained filter membranes used for sterilization. The addition of the test substance in appropriate concentrations to the cultured cells and the maintaining medium forms a series of individual reaction mixtures, each of which is varied only by the concentration of the test substance present in the well.

6. After the series of individual reaction mixtures are formed, all of the cultured cells under test in each well of the multiwell plate are incubated at 37° C. preferably in an atmosphere of 5% $CO_2$/95% air under saturating humidity. During this incubation time, it is desired and preferred that the cultured cells employed in the test be maintained in an atmosphere most advantageous for survival and growth of that cell line. The incubation period preferably is in the range of from 10–14 days' duration, although shorter periods of incubation are useful under specific circumstances. The 10 day incubation period is considered optimal in order to allow sufficient proliferation of the cells serving as controls so that substantial differences among the positive and negative controls and the test cell suspensions may exist on a regular and recurring basis.

7. After the preferred incubation period of 10–14 days has elapsed, the cells from each test and control well are individually harvested and counted. Cells are harvested using a lysing solution such as 10% zapoglobin (Coulter Electronics, Hialeah, Fla.) that disrupts the plasma membranes while leaving the cell nuclei intact without clumping. A preferred lysing solution comprises 10% zapoglobin, 0.5% Triton X100, 2 mM mg $Cl_2$, and 15 mM NaCl in 5 mM phosphate buffer, pH 7.4. The nuclei suspensions are individually counted using an efficient cell counter (Coulter Counter Apparatus, model ZF) and the cell numbers per well (mean±standard deviation) plotted on a logarithmic scale and correlated against time in days.

8. To obtain reproducible, accurate, and reliable data consistently using this protocol, a series of quality assurance measures should be employed. Under the described preferred conditions, the cell number per well obtained from the control containing $3 \times 10^{-11}$M estradiol should preferably be about tenfold higher than the cell numbers obtained in those reaction mixtures which did not contain any estradiol. These goals are achieved using the optimal 10 day incubation period. In addition, a separate performance estimate should be obtained by measuring the proliferation rate of a separate $10^4$ cell innoculum in a 20% CDHS with and without estradiol in a $3 \times 10^{-11}$M concentration. From this innoculum, cells are harvested every 48 hours (preferably as triplicate samples) for the entire 10 day incubation period. A good estimate of the proliferation rate is the mean generation time, "$t_D$". "$t_D$" is defined as the time interval in which an exponentially growing culture doubles its cell number. $t_D$ is calculated from the equation $\alpha = 1/t \ln C_t/C_o$, where $C_o$ is the initial cell number, $C_t$ is the cell number at time=t, and $\alpha$ is the instantaneous cell proliferation constant ($t_D$ is the value $\ln Ct/Co \times \alpha$ would have when $C_t = 2C_o$). "$t_D$" is expressed in time units, i.e., hr.. The slopes of the different growth curves are calculated by fitting the experimental data to a straight line by regression analysis of the pairs in cell numbers/time. $t_o$ is defined as the moment at which the seeding medium is replaced by the maintaining medium. In these conditions, the doubling time ($t_D$) of C7MCF7-173 is 36h for the cultures in 20% CDHS+$3 \times 10^{-11}$ME2, and 300 h for the control (estrogenless) cultures.

9. The interpretation of the empirically derived data in which the number of cultured cells present in each of the incubated reaction mixtures is determined, is directly based on the premise that a measurable increase in the number of cultured cells in those reaction mixtures containing the test substance identifies the substance under test as an estrogen agonist. In other words, the substance under test has empirically demonstrated the ability to interact with the endogenous inhibitor present in charcoal-dextran stripped human serum and has neutralized the effects of the endogenous inhibitor in such degree that the cells proliferate. The ability to interact and neutralize the effect of the endogenous inhibitor present in the CDHS in a partial or complete degree also serves to identify the substance under test as a full agonist or as a partial agonist. The differences are illustrated by the data represented in FIG. 1.

Figure 1:
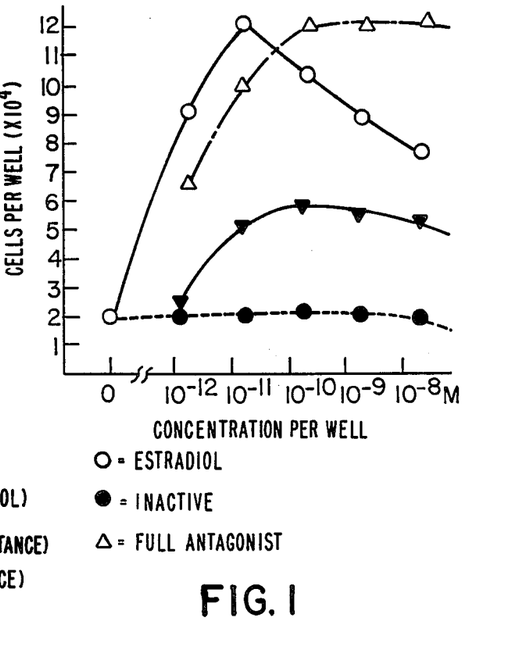
FIG. 1 is a graph illustrating the interpretative basis for assessing empirical data to determine whether a substance is an estrogen agonist.

As is revealed by the graph of FIG. 1, the basis of comparison is the demonstrated ability of estradiol to induce proliferation of the cell line in-vitro and is empirically provided by the data in the control wells. A test substance tested in the manner similar to that for estradiol in this protocol, will demonstrate one of three different growth phenomena: as a full or complete agonist which behaves in a manner similar to estradiol although the maximum effect may occur at a use concentration above or below the maximal growth effect induced by estradiol at the $3 \times 10^{-11}$M concentration; as a partial agonist which shows some ability to induce cell proliferation in comparison to the number of cells maintained in the control wells which do not proliferate at all, but this measurable increase never rises to the numerical values comparable to those provided by estradiol itself; and as a quiescent composition which provides no substantial increase in the number of cultured cells over those numbers yielded by the control, and accordingly is said to have no ability to induce or initiate cell proliferation under the test circumstances. In this manner, by comparing the ability of the test substance to initiate or to fail to initiate cell proliferation under the described test circumstances, such agonistic characteristics as are inherent in the substance under test are demonstrated and evaluated on a comparative basis with estradiol.

Phase 2 Testing For Identification Of Estrogen Antagonistic Properties

This test protocol identifies and measures (on a comparative basis) the antagonistic properties of test substances when simultaneously added with estradiol to a prepared cell culture. The protocol is similar to the Phase 1 protocol in: the selection of a cell line for culture in-vitro which is demonstrably estrogen dependent for proliferation in-vivo; the preparation of aliquots of cells which are subsequently seeded into a plurality of wells in a multiwell plate; the use of 5% FBS in DME as a culture medium until the test phase has begun; and the use of 20% CDHS in DME as the preferred maintaining media which contains the endogenous inhibitor at a concentration effective to prevent proliferation in-vitro of the seeded cells in each well.

Accordingly, steps 1 through 3 are performed as stated earlier within the protocol of Phase 1, the full description of each individual step not being reproduced again here. In essence, $10^4$ cultured cells are seeded into each well, test and control. The medium is changed to 20% CDHS in DME as the maintaining medium; and the following combination of estradiol and test substance added to the cultured cells to form a series of reaction mixtures:

(a) $3 \times 10^{-11}$M estradiol;

(b) $3 \times 10^{-11}$M estradiol and $3 \times 10^{-6}$M test substance;

(c) $3 \times 10^{-11}$M estradiol and $3 \times 10^{-7}$M test substance;

(d) $3 \times 10^{-11}$M estradiol and $3 \times 10^{-8}$M test substance;

(e) $3 \times 10^{-11}$M estradiol and $3 \times 10^{-9}$M test substance.

It will be noted that varying concentrations of the test substance ranging from approximately $10^{-6}$ to $10^{-9}$M are combined with one uniform concentration of estradiol, $3 \times 10^{-11}$M. This concentration of estradiol has been found to be most useful in the majority of test instances; however, the use concentration of estradiol in this Phase 2 protocol may be varied to meet the individual user's needs or desires. It is required only that one uniform concentration of estradiol (or other naturally occuring estrogen) be employed in sufficient but not exceedingly higher concentrations than that required for maximal cell proliferation in combination with varying concentrations of the substance under test. For this reason, the preferred concentrations for the subtance to be evaluated are as described; nevertheless, these specific test concentrations may be increased or decreased in accordance with the individual needs or desires of the user.

Subsequent to adding prepared concentrations of the test substance and the estradiol to each of the wells containing aliquots of cells in known quantity to form a series of individual reaction mixtures, each of the reaction mixtures is incubated in the manner identical to that described in the Phase 1 protocol for the preferred period of between 10 and 14 days. As before, the true incubation period of time may be varied; nevertheless it is preferred that the incubation period be not less than 10 days routinely.

After the preselected incubation period has elapsed, the number of cells in each of the wells, test and control, are determined in the manner identical to that described for Phase 1 testing. The cells are harvested with a lysing solution that disrupts the plasma membranes leaving the cell nuclei intact without clumping. The individual nuclei suspensions from each of the wells are then counted separately using a Coulter Counter and the cell number per well (mean±standard deviation) are calculated accordingly. By definition, an antagonist is a substance which when combined with estradiol results in a reduction in the final number of cells in comparison with the final cell count obtained using estradiol alone. The empirically obtained final cell counts from any test series should be interpreted in accordance with the results graphically plotted in FIG. 2.

Figure 2:
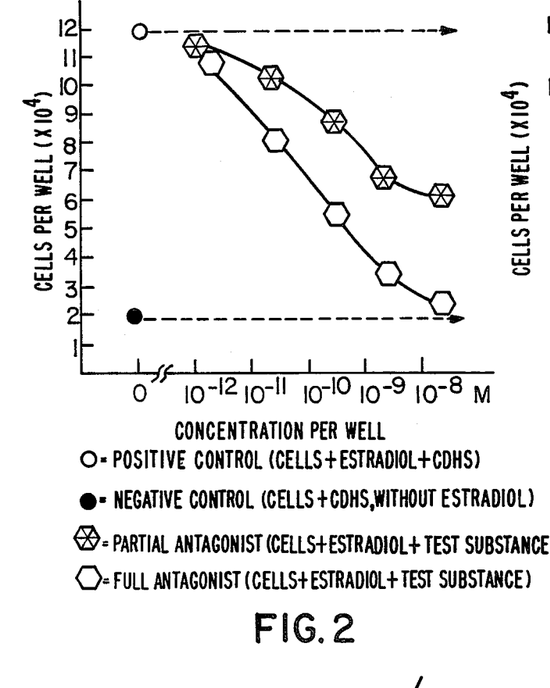
FIG. 2 is a graph illustrating the interpretative data by which a substance may be identified as an estrogen antagonist.

As seen in the graph of FIG. 2, the cultured cells incubated in-vitro in 20% CDHS alone, the negative controls containing no estradiol or test substance whatsoever, maintain a substantially small number. Accordingly, the endogenous inhibitor present in the CDHS inhibits the proliferation of the cells in culture thereby providing a substantially constant number throughout the test period. In comparison, the positive controls comprising 20% CDHS and estradiol without any test substance, provides a much higher number of cells throughout the entirety of the test period, a number about one order of magnitude greater than that of the negative control in a 10 day assay. In comparison to both these positive and negative controls, a test substance combined with estradiol may demonstrate a small decrease in cell number or a substantive decrease in cell number, respectively; a large, substantive decrease in cell number identifies a full or complete antagonist; such a substance is able to lower the cell growth rate from the maximal to the minimal level comparable to the negative controls containing no estradiol whatsoever. Correspondingly, a partial antagonist will decrease the cell growth rate to intermediate values, values lower than the positive control yields containing estradiol alone, yet higher than those of the negative controls containing no estradiol whatsoever. It will be recognized, by the manipulative steps comprising the Phase 2 protocol and by the interpretation of empirical data, that a test substance able to suppress the ability of estradiol to interact with and to neutralize the effects of the endogenous inhibitor present in the serum, is an estrogen antagonist. The degree with which the substance suppresses the effects of estradiol (or any other endogenous estrogen), will identify and characterize the test substance as being either a complete antagonist or merely a partial antagonist. It should be noted that these antagonistic characteristics are separate and distinct from any agonistic properties identified previously using the Phase 1 protocol. The existence of agonistic and antagonistic properties in a single substance is not unusual and is not in any way contradictory or evidence of artifact in the test methodology. To the contrary, the coexistence of properties which identify a single substance as being a partial agonist and simultaneously a complete antagonist to estrogens is a phenomenon well described in the art.

To demonstrate the phenomena of coexisting agonistic and antagonistic properties and to illustrate the accuracy and reproducibility of both the Phase 1 and Phase 2 protocols, a series of illustrative experiments evaluating the variety of pharmacologically active substances which are well known in the literature was undertaken. The substances evaluated as test samples include the following: estradiol; 11-B chloromethyl estradiol; Moxestrol; tamoxifen; LY117018; LY1156758; RU39411; and progesterone. Estradiol is Estra-1,3,5(10)-triene-3,17 diol [U.S. Pat. Nos. 2,096,744; 2,225,419; and 2,361,847] 11B-chloromethyl estradiol is a synthetic derivative of endogenous estradiol. Moxestrol is 11B-methoxy-19-nor-17a-1,3,5(10)-trien-20-yne-3,17 diol [U.S. Pat. No. 3,579,5450]. Tamoxifen is 2-[4-(1,2-diphenyl-1-butenyl) phenoxy]- N,N-dimethylethanamine [Richardson, Nature 212:733 (1966); British Patent No. 1,064,629; French Addition Patent No. 90,418]. LY117018 is a triphenylethylene derivative useful as an antitumor composition [Black et al., Life Sciences 26:1453–1458 (1980)]. LY1156758 having demonstrated antitumor activity [Bloom et al., Br. Med. J. 2:7–10 (1974)]. RU39411 is said to be an antitumor compound by its manufacturer [Roussel-UCLAF, Paris, France]. Progesterone is a hormone secreted by the corpus luteum during the latter half of the menstrual cycle [U.S. Pat. Nos. 2,379,832; 2,232,438; 2,314,185]. Each of these compositions were evaluated using the protocols described earlier for Phase 1 and Phase 2 tests. The results are presented in Table 1 below.

TABLE 1

| Compound | Optimal Test Concentration | Phase 1 Cell Count | Optimal Test Concentration | Phase 2 Cell Count | Characteristics With Respect To Endogenous Estrogens | Intended Primary Use Prior To Testing |
| --- | --- | --- | --- | --- | --- | --- |
| No additions (control) | 0.00 | 20,000 | 0.00 | 20,000 | None | None |
| Estradiol | $3 \times 10^{-11}$ M | 200,000 | $3 \times 10^{-11}$ M | 200,000 | Full Agonist No Antagonistic Activity | Estrogen |
| 11B-Chloromethyl Estradiol | $3 \times 10^{-12}$ M | 200,000 | $3 \times 10^{-12}$ M | 200,000 | Full Agonist No Antagonistic Activity | Estrogen |
| Moxestrol | $3 \times 10^{-12}$ M | 200,000 | $3 \times 10^{-12}$ M | 200,000 | Full Agonist No Antagonistic Activity | Estrogen |
| Tamoxifen | $3 \times 10^{-6}$ M | 60,000 | $3 \times 10^{-6}$ M | 40,000 | Partial Agonist Partial Antagonist | Antitumor Agent |
| LY117018 | $3 \times 10^{-10}$ M | 40,000 | $3 \times 10^{-8}$ M | 20,000 | Partial Agonist Full Antagonist | Antitumor Agent |
| LY156758 | $3 \times 10^{-9}$ M | 50,000 | $3 \times 10^{-8}$ M | 20,000 | Partial Agonist Full Antagonist | Antitumor Agent |
| RU39411 | No effect in range from $10^{-12}$ to $10^{-6}$ M | 20,000 | $3 \times 10^{-11}$ M | 20,000 | No Agonistic Activity Full Antagonist | Antitumor Agent |
| Progesterone | No effect in range from $10^{-12}$ to $10^{-6}$ M | 20,000 | No effect in range from $10^{-12}$ to $10^{-6}$ M | 200,000 | Quiescent: No Agonistic activity No Antagonistic Activity | Hormone |

It will be recognized that the empirical results are expressed as the final cell number obtained per well. The optimal concentration reported in Table 1 is the smallest concentration at which a maximal effect is detected, be it agonistic or antagonistic. By comparing the empirically obtained results of Table 1 with the interpretive graphs of FIGS. 1 and 2 respectively, each of the substances tested is classified as follows: estradiol is a full or complete agonist; 11B-chloromethyl estradiol and Moxestrol both are full agonists; tamoxifen is both a partial agonist and concurrently a partial antagonist; LY117018 is a partial agonist and a full antagonist; LY156758 is a partial agonist and a full antagonist; RU39411 has no agonistic activity but is a full antagonist; and progesterone is not active either as an agonist nor an antagonist and for this reason is said to be quiescent. It will be recognized and appreciated that the characteristics identified for each of the substances under test in Table 1 correspond to the reports in the published literature regarding their pharmacological characteristics with respect to naturally occurring estrogens. The ability of the present invention to accurately identify and distinguish between estrogen agonists and estrogen antagonists in a wide variety of substances is thus deemed to be unequivocally demonstrated.

As a practical matter, it should be recognized that the empirical results presented in Table 1 are based on the use of 20% CDHS prepared as described earlier herein. While it is theoretically possible to use 100% serum taken from humans which has been adsorbed with charcoal-dextran, this is deemed impractical because such concentrated serum must be dialysed to equilibrium against the fluid comprising the maintaining medium (preferably DME) to provide the nutrients and vitamins necessary for cell survival and multiplication during the incubation period of the test protocol. The 20% concentration of serum is preferred because this concentration provides consistent results and is much more economical than higher concentrations. Other CDHS concentrations up to 40% provide comparable or better results depending upon the sensitivity of the cells in culture to the endogenous inhibitor in the serum; accordingly, the control values for those cells unable to proliferate are usually lower in number when higher concentrations of CDHS are used, but this is not a significant factor so long as consistency of CDHS concentration chosen is maintained throughout the test methodology as a whole.

Qualitative Assay

The phase I and II assays may be read by visual comparison of the cell density achieved by similar inocula grown with different test compositions. The assay protocol follows exactly the descriptions of the quantitative assays already described. The only modification is that by the end of the incubation period, the cells are not harvested. Instead, the cells are fixed and stained "in situ" as described below.

1. The medium in each well is aspirated; each well is carefully rinsed with phosphate-buffered saline solution (50 mM Na phosphate buffer, pH 7.0, 150 mM NaCl or comparable isotonic solution).

2. The isotonic solution is removed by aspiration, and 1 ml 10% formalin in phosphate-buffered saline (or comparable isotonic buffer) is placed in each well. This solution will fix the cells in a 3 minute incubation period. After fixation, the formalin solution is removed by aspiration.

3. 1 ml of 0.01 N sodium hydroxide is placed in each well, and aspirated after 30 seconds—1 minute interval.

4. 0.5 ml of a 0.5% crystal violet aqueous solution is pipetted into each well, and removed by aspiration after 1 minute.

5. The plates are washed with tap water until the background is clear.

6. The plates are dried by placing them upside down on an adsorbent mat.

Figure 6:
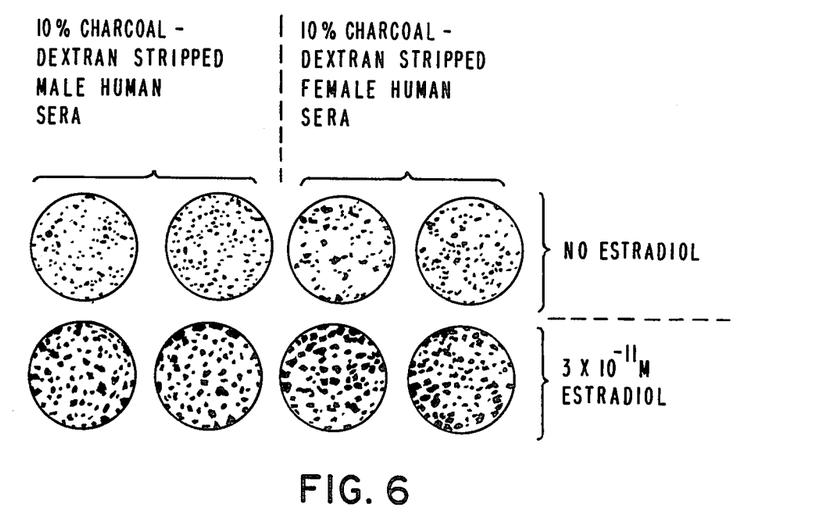
FIG. 6 illustrates the actual visual display resulting from the culture of MCF7 cells for 10 days in a medium containing charcoal-dextran stripped human male and female sera at 10% concentration.

7. The results may be recorded by xerox copy as shown in FIG. 6.

Alternatives To The Use Of CDHS

Functional equivalents of CDHS in the maintaining medium may be employed in either Phase 1 and/or Phase 2 protocols freely as desired. The maintaining medium used in the test protocols is required to contain only two essential components; a fluid carrier, preferably DME, containing a requisite amount of nutrients, vitamins, salts, and the like to maintain the cell culture in a healthy, viable state; and a measurable concentration of an inhibitor endogenous to the serum of adult male and female humans which is present in the fluid at a concentration effect to prevent the proliferation of the cells in-vitro. Both essential requirements are satisfied by the use of CDHS in more than 5% final concentration by volume. Alternatively, the maintaining medium may comprise any of the well known natural or synthetic preparations now available for the maintenance of cells in culture in combination with a predetermined quantity of concentrated, semi-purifed, proteinaceous inhibitor which has been isolated from the plasma of adult humans.

Protocol For Isolation Of Purified Inhibitor Able To Prevent Proliferation Of Estrogen Dependent Cells In-Vitro 1. Source: It is preferred that outdated frozen plasma from adult humans be used. The plasma is not to be kept at 4° C. for more than 24 hours from the time it was drawn until the moment it is utilized in the purification protocol.

This precaution is taken to avoid degradation of the inhibitor by the serine proteases present in plasma. Serum may be employed in lieu of plasma if desired; however, outdated plasma is preferred because of its lesser cost.

2. Removal of coagulation factors: To the plasma sample maintained at 4° C. estradiol is added at a concentration of 100 picograms ($10^{-12}$ grams) per ml of plasma. To this mixture 1.0M sodium citrate solution is added until a total volume concentration of 15 mM is obtained. To this total volume 1.0M benzamidine is added until a final concentration of 5.0 mM is achieved. Subsequently, a 1.0 M $BaCl_2$ solution is added very slowly in sufficient quantity to achieve a final volume concentration of 80 mM in the fluid mixture. With the addition of $BaCl_2$ solution, a precipitate is formed which is stirred very gently to form a suspension. The reaction mixture is then placed in a container having an air-tight closure and positioned on a roller apparatus (Bellco Co., Vineland, N.J.), and rotated for approximately 60 minutes at 4° C. Subsequently, the reaction mixture is centrifuged at 3000×gravity for 10 minutes to form a supernatant and a precipitant layer. After separating the fractions, the precipitant is discarded and the supernatant fraction combined with ammonium sulfate.

3. Ammonium sulfate precipitation: Initially, the supernatant is brought to a 55% saturation concentration of ammonium sulfate. This is achieved by adding 0.351 grams of crystaline ammonium sulfate to each milliliter of supernatant fluid. The ammonium sulfate crystals are first prepared as regular, pulverized particles using a mortar and pestle. These small crystals are added slowly to the supernatant at 4° C. with gentle stirring of the mixture. Precipitation is allowed to proceed for 30 minutes duration while the fluid is held at 4° C. The precipitated material is then isolated by centrifugation at 10,000×gravity for 15 minutes. The supernatant fluid is retained while the pellet of precipitated material is discarded.

Subsequently, the supernatant fluid is brought up to a 70% saturation of ammonium sulfate. The supernatant fluid is then combined with an additional 0.01 grams of ammonium sulfate per milliliter of fluid with gentle mixing while the crystalline material is being added. This results in a second precipitant being formed which is isolated by centrifugation of the mixture at 10,000×gravity for 15 minutes duration. The isolated precipitant contains the active inhibitor which is isolated by resuspending the precipitant material in 50 uM Tris buffer pH 7.0 containing 5.0 mM benzamidine. Alternatively, the precipitated pellet material may be stored indefinitely at −70° C. in 70% saturated ammonium sulfate solution.

When the ammonium sulfate precipitated inhibitor is to be utilized, it is necessary to remove the excess salt by dialysis against a buffer suitable for use in tissue culture, such as 25 mM Hepes buffer containing 100 mM NaCl, pH 7.4. The preferred ratio of inhibitor to dialysate fluid should be in the order of 1:50 by volume. In the preferred method, the dialysis step is performed with two changes of Hepes—NaCl buffer.

This method of preparation results in a 3–5 fold purification with a 60–70% yield of inhibitor protein. It should be noted that the inhibitor protein may degrade over time; accordingly, the inhibitor is preferably kept in a 70% ammonium sulfate saturated solution containing 5 mM benzamidine until the time of use.

Assay To Determine The Potency Of The Concentrated Inhibitor

The potency of the inhibitor isolated from human serum is defined in activity units. An activity unit is defined as that amount of purified inhibitor protein required in 1.0 ml of medium to increase the doubling time of a $10^4$ cell innoculum (the time required for a cell concentration to double in quantity) by a factor of 2 at the end of a 9 calendar day period. To determine the potency of any preparation comprising purified inhibitor, the following measurements should be performed, preferably in duplicate using simultaneously seeded wells:

Procedure I: Determination of the optimal proliferation rate for a $10^4$ cell innocula in 20% CDHS in combination with $3 \times 10^{-11}$M $E_2$ (for C7MCF7-173 cells the expected optimal rate is 36–37 hours).

Procedure II: Determination of the standard dose-response curve to different concentrations of CDHS in combination with varying concentrations of estradiol such as (a) no estradiol and (b) $3 \times 10^{-11}$M estradiol.

Procedure III: Determination of the dose-response curve to different concentrations of $(NH_4)_2SO_4$ precipitated inhibitor preparations which have been added to 5% charcoal-dextran stripped fetal bovine serum, hereinafter "CDFBS" (containing no detectable quantity of endogenous inhibitor) in combination with varying concentrations of estradiol such as (a) no estradiol and (b) $3 \times 10^{-11}$M estradiol.

Figure 3:
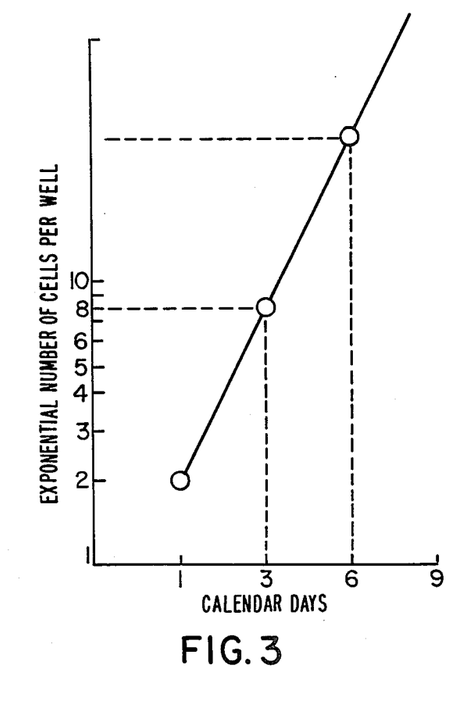
FIG. 3 is a graph showing the exponential growth rate of cells in culture.

To perform Procedure I, $10^4$ cell innocula preferably are seeded in 5% FBS into each well as described in the Phase 1 and 2 assay protocols. 24 hours later, the medium is changed to 1.0 ml per well of 20% CDHS containing $3 \times 10^{-11}$M estradiol. Triplicate cultures of cells are harvested on calendar days 1, 3, 5, 7, and 9 of the test period. The numerical cell count data are plotted using a log-linear scale as shown in FIG. 3. From the graphic data plot, the doubling time is extrapolated.

To perform Procedures II and III, innocula comprising $10^4$ cells in 5% FBS are seeded into a series of wells. 24 hours later, the medium is changed: 1.0 ml per well of 5%, 10%, 20%, or 40% CDHS respectively (preferably as duplicate samples) for Procedure II; and 1.0 ml per well of different concentrations of the precipitated inhibitor preparation in 5% CDFBS for Procedure III. All cell cultures are then harvested and counted on the 9th day of the test period in accordance with the methods described for the Phase 1 and 2 protocols.

From the empirically obtained cell count data, a determination of how many times the cells in each innocula have doubled during the nine calendar days in culture is made with respect to: the different concentrations of serum (Procedure 2); or to the different concentrations of precipitated inhibitor preparation (Procedure 3). This determination is made as follows:

(i) the number of cells in the innocula at the beginning of the experiment are obtained from Procedure 1 (the cell number on day 1).

(ii) the number of cells in existence on day 9 of the test are taken from the series of samples comprising Procedures II and III respectively. The maximal number of cells is taken from the count of Procedure I, day 9.

(iii) the number of doublings for the cell innocula is calculated by the term:

$$3.3 \times (\log \text{cell no. at day } 9 - \log \text{cell no. at day } 1)$$

Figure 4:
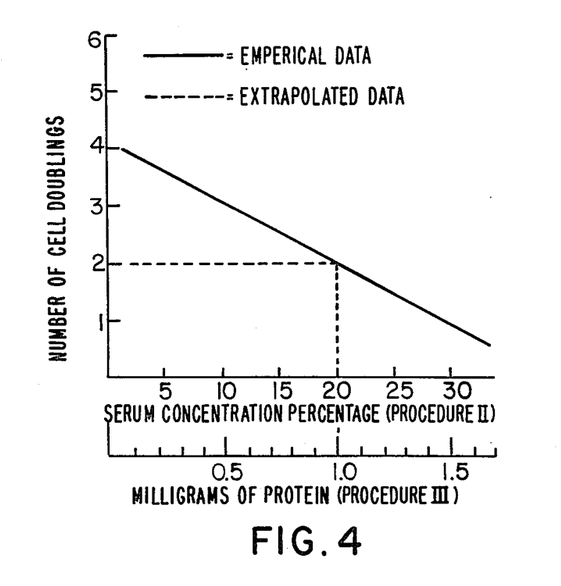
FIG. 4 is a graph illustrating the correlation between number of cell doublings as a function of inhibitor activity.

As may be seen in FIG. 4, the concentration of inhibitor protein at which the number of cell doublings achieved is half maximal represents 1 unit of inhibitory activity. For CDHS, this value is attained at 15–20% concentration; accordingly there are 5–6 units of inhibitor per ml of undiluted serum, or 0.07 units per mg protein. The preferred concentration for use in the Phase 1 and Phase 2 protocols is thus 20% serum—the equivalent of 1 unit per ml of inhibitor in the maintaining medium. Mathematically this is stated as:

$$1 \text{ unit} = \frac{3.3 \,(\log \text{cell no. at day } 9 - \log \text{cell no. at day } 1)}{2}$$

Figure 5:
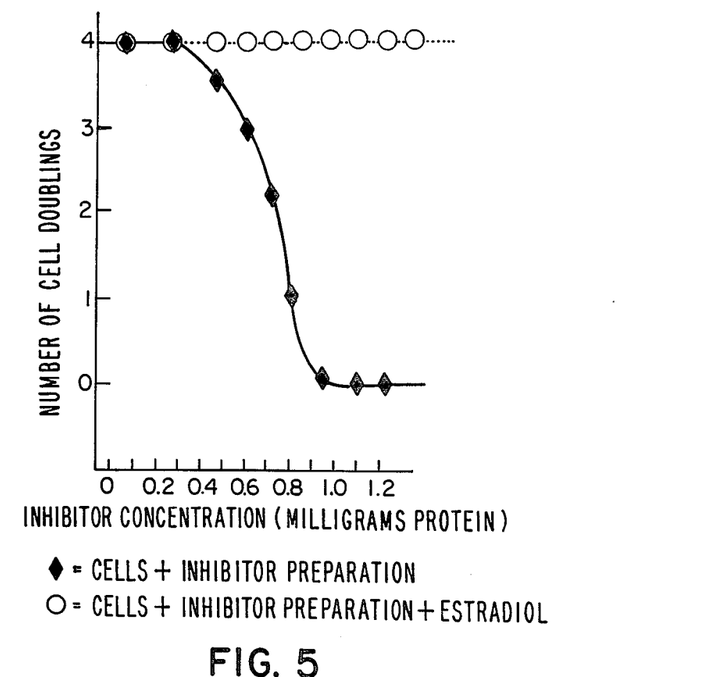
FIG. 5 is a graph illustrating the ability of estradiol to neutralize the activity of the inhibitor.

(iv) A comparison of the total cell number at each inhibitor concentration, in the presence [(b) series] and absence [(a) series] of estradiol may now be made. Such a comparison is graphically illustrated by FIG. 5. The graphic comparison establishes whether or not the precipitated preparation contains an active inhibitor which is able to be neutralized by estradiol; and whether or not spurious toxic materials are present in the preparation. In the latter instance, the action of the inhibitor is not reversed by endogenous estrogens.

It is specifically noted that the quantitative difference between the cell count data obtained in the presence and absence of estradiol at set concentrations of inhibitor above the equivalent effect of 5% CDFBS should be between 5 and 10 fold; i.e., those cells without any estradiol should achieve no more than one half the number of doublings achieved by those innocula receiving estradiol.

Final Considerations

It will be recognized that a major advantange of the described in-vitro methods is the ability to identify a substance as having agonistic or antagonistic properties in comparison to endogenous estrogens. Based on this ability, the protocols can serve as an initial screening determination to characterize presently available or newly synthesized compositions for their primary or secondary side effects. For example, the present invention will evaluate new compounds whose intended use are as pesticides; as intermediate or final compositions suspected of having estrogen-like effects due to their manufacturing process; as therapeutic drugs which might have undesirable side effects in addition to their primary pharmacological effect; and as antitumor (anticancer) agents which are suspected of having unwanted agonistic properties in addition to the desired antagonistic properties with respect to endogenous estrogens. As an example of the last instance, the use of the drug tamoxifen for the clinical treatment of estrogen sensitive breast cancers in women is dependent upon this drug behaving as a partial agonist and as a partial antagonist with respect to the estrogens in the body. Ideally, the most powerful anticancer compositions against estrogen-sensitive tumors should demonstrate not only total inactivity as an agonist but also full antagonistic activity against estrogens. Using the present methodology, a wide variety of compositions could be initially identified and evaluated prior to being utilized in clinical field trials involving human subjects. The invention is not to be restricted in form nor limited in scope except by the claims appended hereto.

What we claim is:

1. An in-vitro method for identifying a substance of interest as an in-vivo estrogen agonist, said method comprising the steps of:
   obtaining a plurality of cells cultured in-vitro, said cells being estrogen dependent for proliferation in-vivo;
   maintaining a known quantity of said cultured cells in a medium without estrogens comprising a fluid and an inhibitor of cell proliferation endogenous to the serum of adult humans, said endogenous inhibitor being present in said maintaining medium at a concentration effective to prevent proliferation of said cells in-vitro in the absence of an estrogen;
   adding the substance of interest to said cultured cells in said maintaining medium to form a reaction mixture;
   incubating said reaction mixture for a preselected time period; and
   determining the number of cultured cells in said incubated reaction mixture, a measurable increase in the number of cultured cells identifying the substance of interest as an estrogen agonist.

2. An in-vitro method for identifying a substance of interest as an in-vivo estrogen antagonist, said method comprising the steps of:
   obtaining a plurality of cells cultured in-vitro, said cells being estrogen dependent for proliferation in-vivo;
   maintaining a known quantity of said cultured cells in a medium without estrogens comprising a fluid and an inhibitor of cell proliferation endogenous to the serum of adult humans, said endogenous inhibitor being present in said maintaining medium at a concentration effective to prevent proliferation of said cells in-vitro in the absence of an estrogen;
   adding the substance of interest and an estrogen to said cultured cells in said maintaining medium to form a reaction mixture;
   incubating said reaction mixture for a preselected time period; and
   determining the number of cultured cells in said incubated reaction mixture, the failure of said cultured cells to measurably increase in number identifying the substance of interest as an estrogen antagonist.

3. An in-vitro method for identifying a substance of interest as having in-vivo estrogen agonistic and estrogen antagonistic properties, said method comprising the steps of:
   obtaining a plurality of cells cultured in-vitro, said cells being estrogen dependent for proliferation in-vivo;
   maintaining a known quantity of said cultured cells in a medium without estrogens comprising a fluid and an inhibitor of cell proliferation endogenous to the serum of adult humans, said endogenous inhibitor being present in said maintaining medium at a concentration effective to prevent proliferation of said cells in-vitro in the absence of an estrogen;
   adding the substance of interest to a first aliquot of said cultured cells in said maintaining medium to form a first reaction mixture;
   adding the substance of interest and an estrogen to a second aliquot of said cultured cells in said maintaining medium to form a second reaction mixture;
   incubating said first reaction mixture and said second reaction mixture for a preselected time period;
   determining the number of cultured cells in said incubated first reaction mixture, a measurable increase in the number of cultured cells identifying the substance of interest as an estrogen agonist; and
   determining the number of cultured cells in said incubated second reaction mixture, the failure of said cultured cells to measurably increase in number identifying the substance of interest as an estrogen antagonist.

4. The in-vitro method as recited in claim 1, 2, or 3 wherein said cultured cells comprise tumor cells derived from the female human breast.

5. The in-vitro method as recited in claim 4 wherein said cultured cells are C7 MCF7-173 cells, having ATCC accession number CRL 9836.

6. The in-vitro method as recited in claim 2 or 3 wherein said estrogen is selected from the group consisting of estrone, estradiol, and estriol.

7. The in-vitro method as recited in claim 1, 2, or 3 wherein said maintaining medium comprises fetal bovine serum.

8. The in-vitro method as recited in claim 1, 2, or 3 wherein said maintaining medium comprises Dulbecco's modification of Eagle's Minimal Essential Medium.

9. The in-vitro method as recited in claim 1, 2, or 3 wherein said maintaining medium comprises charcoal-dextran stripped human serum.

10. The in-vitro method as recited in claim 9 wherein said serum is used in a concentration ranging from 40-10% concentration by volume.

11. The in-vitro method as recited in claim 1, 2, or 3 wherein said wherein said inhibitor is added to said maintaining medium as a incompletely proteinaceous preparation.

12. The in-vitro method as recited in claim 1, 2, or 3 wherein said reaction mixtures are incubated for a time period ranging from 9-14 calendar days.

13. The in-vitro method as recited in claim 1, 2, or 3 wherein said fluid of said maintaining medium comprises at least one selected from the group consisting of buffers, amino acids, sugars, vitamins, and ionizable salts.

* * * * *